United States Patent [19]

Terry, Jr. et al.

[11] Patent Number: 5,540,730
[45] Date of Patent: Jul. 30, 1996

[54] TREATMENT OF MOTILITY DISORDERS BY NERVE STIMULATION

[75] Inventors: Reese S. Terry, Jr.; Ross G. Baker, Jr., both of Houston, Tex.; Andre Marquette, Stamford, Conn.

[73] Assignee: Cyberonics, Inc., Webster, Tex.

[21] Appl. No.: 469,174

[22] Filed: Jun. 6, 1995

[51] Int. Cl.$^6$ .................................................... A61N 1/05
[52] U.S. Cl. ........................................................... 607/040
[58] Field of Search .................................. 607/2, 40, 133

[56] References Cited

U.S. PATENT DOCUMENTS

| | | | |
|---|---|---|---|
| 3,334,792 | 10/1967 | Offner. | |
| 4,867,164 | 9/1989 | Zabara. | |
| 5,025,807 | 6/1991 | Zabara. | |
| 5,188,104 | 2/1993 | Wernicke. | |
| 5,231,988 | 8/1993 | Wernicke. | |
| 5,263,480 | 11/1993 | Wernicke | 607/118 |
| 5,269,303 | 12/1993 | Wernicke | 607/45 |
| 5,292,344 | 3/1994 | Douglas | 607/40 |
| 5,423,872 | 6/1995 | Cigaina | 607/40 |

FOREIGN PATENT DOCUMENTS 344920A 6/1989 European Pat. Off. ......... A61N 1/40

*Primary Examiner*—William E. Kamm
*Assistant Examiner*—Scott M. Getzow
*Attorney, Agent, or Firm*—Wigman, Cohen, Leitner & Myers, P.C.

[57] ABSTRACT

Apparatus for treating patients with motility disorders applies a modulating signal to the patient's vagus nerve to stimulate or inhibit neural impulses and produce excitatory or inhibitory neurotransmitter release by the vagus nerve according to the specific nature of the motility disorder. The apparatus includes a neurostimulator which can be activated to generate an electrical output signal. The neurostimulator is responsive to the sensing of a selected event having occurred which is indicative of the need for treatment of the motility disorder, and includes an activation element which responds to sensing of that event to activate the neurostimulator, and a lead with an electrode array to apply the electrical output signal as the modulating signal to the patient's vagus nerve. Certain parameters of the output signal are programmable, and the neurostimulator can be calibrated according to the specific patient and the specific motility disorder being treated. One form of sensor detects the impedance of a selected part of the gastrointestinal system to detect the presence of excessive contractions in that part as an indication of hypermotility whether or not food has been consumed by the patient within a preset interval of time, and inadequate contractions in that part as an indication of hypomotility if food was consumed by the patient within a preset interval of time.

21 Claims, 2 Drawing Sheets

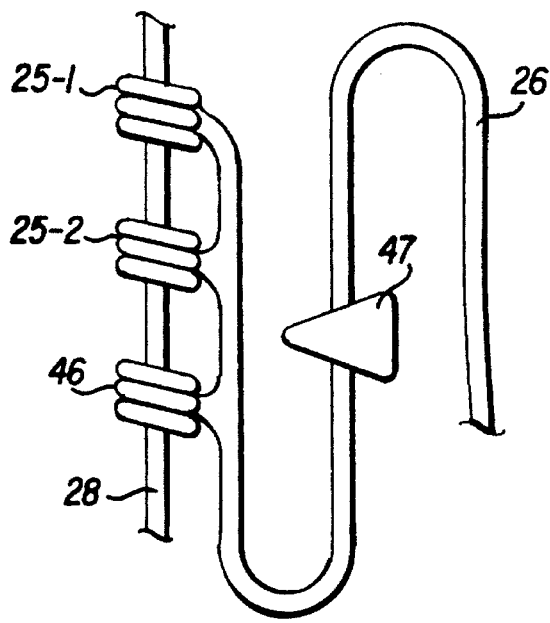
FIG. 4
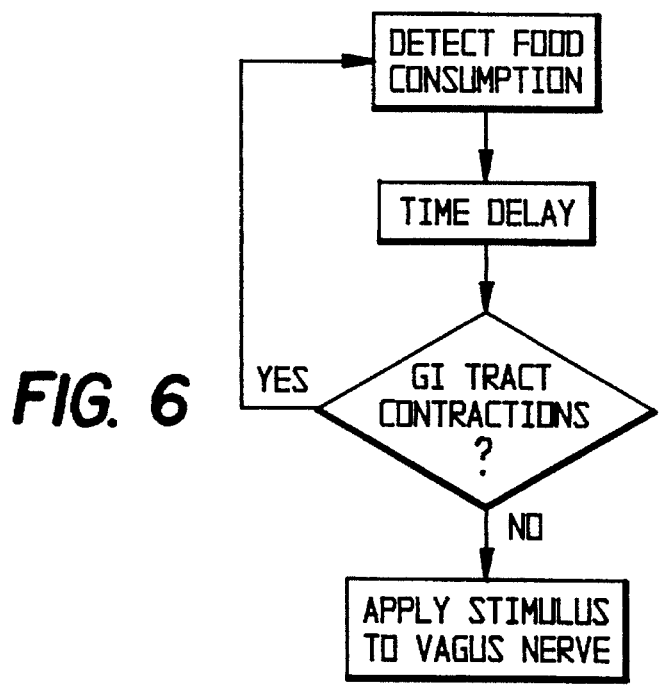
FIG. 6
FIG. 5
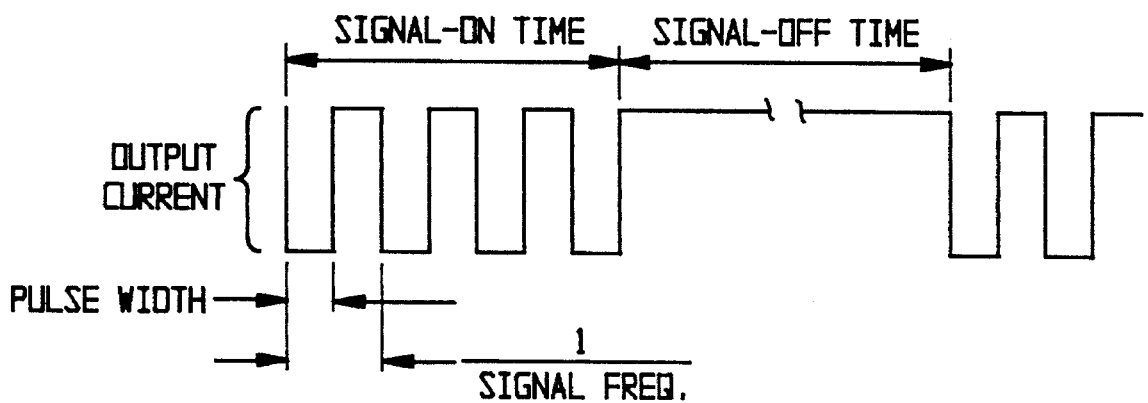

TREATMENT OF MOTILITY DISORDERS BY NERVE STIMULATION

BACKGROUND OF THE INVENTION

The present invention relates generally to methods and apparatus for treating or controlling medical, psychiatric or neurological disorders by application of stimulating electrical signals to a selected nerve or nerve bundle. More particularly, the invention resides in techniques for treating patients who suffer from chronic motility disorders of the gastrointestinal system, by selectively modulating electrical activity of the vagus nerve.

The digestive system functions to allow nutrients and other food substances to be processed in a manner for efficient absorption by the cells of the body. Food is ingested, large particles are broken into smaller particles, enzymes are secreted to decompose food molecules, the products of the digestive action are absorbed, and unused residue is eliminated. In the alimentary canal of the digestive system, food and materials which are by-products of the digestive process are moved along by peristalsis—movement resulting from waves of alternate circular contraction and relaxation of the tubular structure of the canal by which the contents are propelled onward.

In the context of the present invention, motility consists of normal spontaneous distensions and contractions of the stomach, intestines, and other portions of the canal to move food through the gastrointestinal tract during the digestive process, and related activity. The disorders of interest for treatment according to the invention include hypomotility, in which contractions are not occurring naturally or are abnormally slow; and hypermotility, which is characterized by abnormally rapid contractions.

Chronic hypomotility disorders of the stomach involve gastric stasis (stagnation of fluids), or delayed gastric emptying. Hypomotility is commonly associated with chronic medical conditions such as gastric ulcer, gastroesophageal reflux (regurgitation of the contents of the stomach into the esophagus), diabetic gastroparesis (a slight paralysis of the muscular coat of the stomach), postvagotomy (attributable to effects of excising part of the vagus nerve in treating chronic ulcer patients), and postgastrectomy (following excision of part of the stomach). The disorder has been classified as being of unknown cause (idiopathic) in some 50% of the cases (M. Sleisenger et al., *Gastrointestinal Disease*, 4th ed., HBJ, Inc., Phila., 1989, pp. 675–713).

Current forms of therapy for such hypomotility include treatment of the underlying disorder, dietary support, use of drugs with prokinetic agents such as metoclopramide, and surgery. The long term therapeutic value of metoclopramide in patients with idiopathic gastric stasis or gastric ulcer has not been established (Sleisenger et al., ibid.). Further, a loss of effectiveness of the drug's gastrokinetic properties has been observed in long term use for treating diabetic gastroparesis (R. Schade et al., *Dig.Dis.Sci.*, 1985, Jan., 30(1), pp. 10–15).

Chronic hypermotility disorders of the stomach involve a dumping syndrome characterized by epigastric pain, nausea, vomiting, diarrhea, and weakness which typically occur within thirty minutes after meals. The dumping syndrome is commonly associated with chronic postgastric surgical conditions, such as gastroenterostomy (in which a new opening is established between the stomach and intestine), partial gastrectomy, vagotomy with pyloroplasty or antrectomy, and proximal gastric vagotomy. Therapies currently applied for this disorder similarly include dietary support, use of drugs (anticholinergic agents), and remedial surgery.

In contrast, motility disorders of the intestines are commonly associated with chronic medical conditions such as duodenal ulcer (in the small intestine), irritable colon syndrome or diverticulosis (in the large intestine), and diabetes. Often, the disorder is diagnosed as idiopathic. As in the cases of the stomach motility disorders, drug therapy is the treatment of choice for the intestinal variety - cholinergic agents for small intestine motility, and metoclopramide for large intestine motility.

Metoclopramide is most often prescribed among motility patients because hypomotility is more common than hypermotility. At least one study has indicated that this drug is effective in only 60% of patients with diabetic gastroparesis, and in only 25% of patients with prior gastric surgery (e.g., *Drug Evaluations*, 6th ed., AMA, Chicago, 1986, p. 953). As noted above, evidence also exists that the effectiveness of metoclopramide dissipates with long term use. This appears to be the case at least where diabetes is the underlying disease (Schade et al., ibid). The long term value of the drug has not been established for treating gastric stasis which is either idiopathic or attributed to gastric ulcer.

Another reported disadvantage of metoclopramide therapy is that 20% of user patients experience side effects of drowsiness, restlessness, or anxiety (see M. Sleisenger et al., id.).

A principal aim of the present invention is to provide a new and improved therapy for treating motility disorders which is not only safe and effective but avoids the undesirable side effects that have characterized known treatments such as drug therapy.

According to the invention, motility disorders of the gastrointestinal (GI) system, and especially chronic hypermotility and hypomotility of the stomach, are treated and controlled using vagus nerve stimulation to selectively and controllably modulate the nerve's electrical activity in a predetermined manner to inhibit or stimulate motility of the affected region, according to need.

The vagus nerve plays a substantial role in innervation of the GI tract (S. Ritter, *Neuroanatomy and Physiology of Abdominal Vagal Afferents*, CRC Press, Florida, 1992, at pages 23 et seq.). Neuroanatomical studies have demonstrated that structures in the central vagal complex, such as the nucleus ambiguus, act as a synaptic point for special visceral efferents of the vagus nerve that innervate striated muscle of the upper GI tract. Also, structures in the dorsal vagal complex, such as the dorsal motor nucleus (DMN), act as a synaptic point for general visceral efferents of the vagus nerve that make synaptic contact with postganglionic neurons in the myenteric plexus of the bowel wall, with connection to the smooth muscle of the GI tract.

In the rat, motor neurons of the DMN begin innervating the GI tract at the stomach, and continue as far as the descending colon. Afferent information from the GI tract travels to higher brain nuclei through the vagus nerve (Ritter, ibid.). Gastric emptying can be inhibited by cholecystokinin (CCK) (K. Kelly, *Am.J.Physiol.*, 239, 1980, at G71–G76), a hormone released from the intestinal wall in the presence of fats in the upper part of the small intestine. CCK bonds with central receptors that lie in the nucleus of the solitary tract connected to the GI tract by the vagus nerve. The action of CCK decreases gastric motility as the small intestine fills with food. The vagus nerve thus plays an important role in transmitting efferent and afferent signals between the higher brain structures and the GI tract.

Two groups of efferent fibers in the vagus-enteris reflex can either increase or decrease gastric motility, and, in some species, can be differentiated based on threshold of electrical stimulation. The excitatory pathway consists of preganglionic cholinergic neurons, releasing acetylcholine that contracts gastric smooth muscle. The vagal inhibitory fibers consist of a cholinergic preganglionic neuron that synapses onto a non-adrenergic, non-cholinergic myenteric neuron. The vasoactive intestinal peptide may be the transmitter used by these neurons (J. H. Meyer, *Physiology of the Gastrointestinal Tract*, L. R. Johnson ed., Raven Press, N.Y., 1987, pp. 613–629).

Historical data indicates that electrical stimulation of the central cut end of the vagus nerve inhibited ongoing gastric contractions in dogs, cats, rabbits and monkeys (W. J. Page May, *J. Physiol.*, 1904, 31, pp. 261–271), and also that electrical stimulation of peripheral cut stumps of the vagus nerve results in activation of efferent fibers which can produce both inhibition and excitation of gastric motility (B. A. McSwinney, *Physiol. Rev.*, 1931, 11, pp. 478–514). Chemical stimulation of the dorsal vagal complex and the nucleus ambiguus produced gastric contractility in the rat which was interrupted by cutting the vagus nerve (T. Garrick et al, *Am. J. Physiol.*, 256 (6 pt 1):G1011–5, June 1989; P. J. Hornby et al, *Am. J. Physiol.*, 258 (4 pt 1):G637–47, April 1990). Electrical stimulation of the dorsal motor nucleus of the vagus nerve with 100 microA, 50 Hz and 0.2 ms pulse duration increased gastric contractions without affecting gastric acid secretion (H. S. Feng, *Am. J. Physiol.*, 259 (2 pt 1)G321–6, August 1990).

The vagus nerve can also influence motor activity of the small intestine. Peripheral stimulation of an intact cervical vagus nerve produced large contractions of the jejunum and stomach (T. Neya et al, *Brain Res.*, May 28, 1990, 517 (1–2):64–8). Psychologically stressed dogs experienced hypermotility in the jejunum and the duodenum which was eliminated by vagotomy (M. S. Muelas, *Rev. Esp. Enferm. Dig.*, June 1992, 81(6):383–7).

The vagus nerve also influences motor activity of the colon. Vagal efferent stimulation in monkeys increased contractile frequency at all sites in the colon, but after atropine was injected contractile frequency decreased (M. Dapoigny et al, *Am. J. Physiol.*, 262 (2 pt 1):G231–6, February 1992). Stimulation of the hypothalamus or cerebral hemispheres increases or inhibits colonic motility, depending on the area stimulated (Sleisenger et al., id.). Efferent fibers of the vagus respond to gastric distension as well as intestinal distension (L. A. Blackshaw et al, *J. Auton. Nerv. Syst.*, 18, pp. 19–24, 1987; D. Grundy, *J. Physiol.*, 319, pp. 43–52, 1981).

SUMMARY OF THE INVENTION

The present invention takes advantage of the role of the vagus nerve in the digestive process, and its effect upon motility through the GI tract, but does so as a response to sensing abnormal motility characterized by hypomotility or hypermotility. An implanted device is used for nerve stimulation, and in one embodiment is implemented for automatic activation upon sensing a prescribed event indicative of a need for treatment, such as by sensing a particular pattern of contractions at a designated point along the GI tract. In an alternative embodiment, the implanted device is timed for automatic activation (for example, coinciding with each mealtime of the patient, or delayed to approximate the start of the digestive process in the stomach) to stimulate and electrically modulate the electrical activity of the vagus nerve to treat the disorder. In another alternative embodiment, the implanted device is configured to allow manual activation by the patient.

For treating patients suffering from chronic motility disorders, the neurostimulator device of the invention selectively stimulates the vagus nerve in response to sensing of the prescribed event. Preferably, the device is implanted in the patient, and generates an electrical output signal consisting of a sequence of pulses having parameter values, e.g., pulse width and amplitude, which are programmed via telemetry from an external programmer by the attending physician/surgeon after device implantation. The programmed settings of the parameter values are within prescribed ranges deemed appropriate for the treatment, and the resulting signal is applied to the vagus nerve by means of an adjacent nerve electrode or electrode array at the distal end of an implanted lead. The effect is a modulation of the normal electrical activity of the nerve, by stimulation or inhibition, to cause concomitant release or suppression of neurotransmitters according to the desired response. Neurotransmitters are classified as either excitatory or inhibitory. Although the modulating signal may be configured to selectively stimulate or inhibit nerve activity, the term "stimulate" (and its variations) is sometimes used herein in the broader sense to include both.

The specific stimulating signal pattern used to achieve a desired effect of the vagal modulation for a prescribed treatment is selected based on various factors, including individual patient, specific nature of the motility disorder, and nerve fibers to be activated. The stimulation strategy also depends on factors such as whether a symptom or indicator of the disorder can be sensed to activate the neurostimulator, or a physiologic parameter can be detected to trigger the stimulation, and whether a pause or delay after the stimulation interval allows the benefits of the nerve activity modulation to persist.

Accordingly, a more specific aim of the invention is to provide apparatus and methods for treating and controlling motility disorders by selectively stimulating the patient's vagus nerve to modulate electrical activity of the nerve and thereby cause a selective release or suppression of excitatory or inhibitory neurotransmitters that will alleviate the disorder, and in which a symptom or indicator of the motility disorder is sensed for manual or automatic activation of an implanted device for selective modulation.

BRIEF DESCRIPTION OF THE DRAWINGS

The above and still further objects, aspects, features and attendant advantages of the present invention will be better understood from a consideration of the following detailed description of a best mode presently contemplated for practicing the invention as represented by certain preferred methods and embodiments thereof, taken in conjunction with the accompanying drawings, in which:

FIG. 4 is a detailed fragmentary illustration of the nerve electrode installed on the vagus nerve;

FIG. 5 is an illustrative idealized electrical output signal waveform of the stimulus generator; and FIG. 6 is a flow chart to illustrate a device-implemented method of treating a motility disorder.

DESCRIPTION OF THE PRESENTLY PREFERRED EMBODIMENT AND METHOD

A generally suitable form of neurostimulator for use in the present invention is disclosed in U.S. Pat. No. 5,154,172 of R. Terry, Jr., et al. (referred to herein as "the '172 patent"), assigned to the same assignee as the instant application. The specification of the '172 patent is incorporated herein in its entirety by reference, but for the sake of convenience to the reader, certain portions are summarized in this application.

Figure 1:
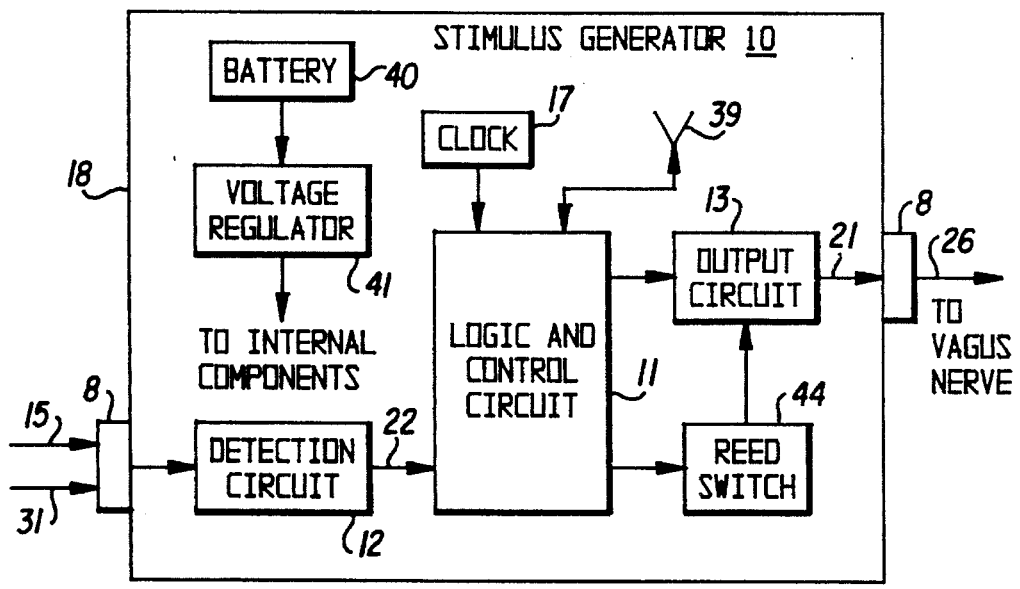
FIG. 1 is a simplified block diagram of an implantable programmable stimulus generator of a neurostimulator for treating motility disorders.

Referring to the drawings, FIG. 1 is a simplified block diagram of the stimulus generator 10 containing the electronics of the implantable neurostimulator. The neurostimulator is microprocessor-based and communicates with an external programmer by asynchronous serial communication to permit control or monitoring of states of the device. The stimulus generator is implanted in the patient's body, preferably in a pocket formed just below the skin in the abdomen (FIG. 2) during implant surgery. In conjunction with its microprocessor-based logic and control circuit 11, the stimulus generator includes detection circuitry 12 (such as a sense amplifier that receives an input signal from a separate sensor located at an appropriate implant site) for automatically initiating generation of a stimulating signal by the generator. An output circuit 13 of the generator configures or patterns the stimulating signal according to programming of the device by the attending physician from an external programmer, to modulate the natural electrical activity of the vagus nerve for treating the motility disorder of interest.

Figure 2:
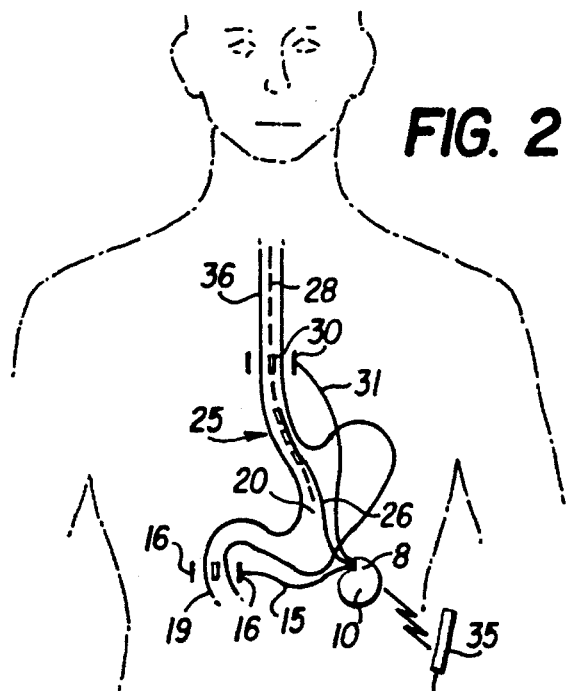
FIG. 2 is a simplified fragmentary illustration of the stimulus generator and lead/electrode system of the neurostimulator implanted in the patient's body.
Figure 3:
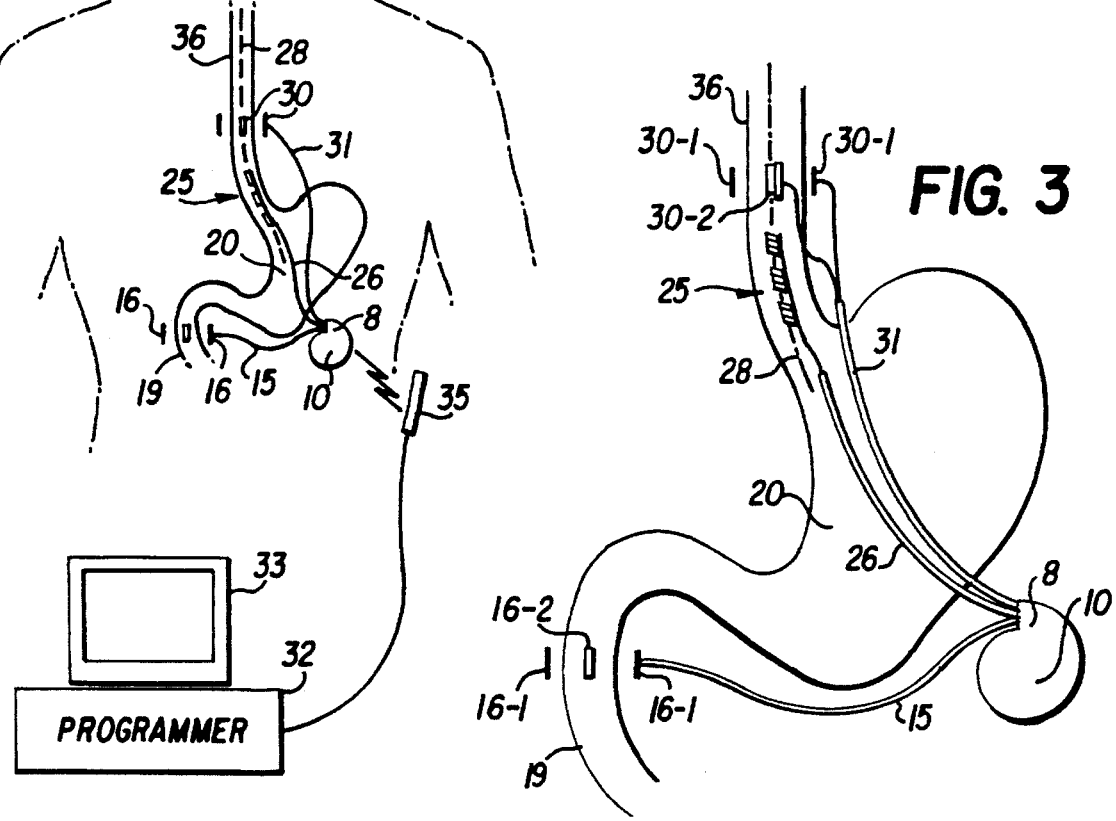
FIG. 3 is a more detailed view of a portion of the preferred embodiment of the stimulus generator and associated lead/electrode system of the neurostimulator illustrating exemplary implant sites.

For example, in a case where treatment of a hypomotility disorder is desired, the detection circuit 12 is coupled to a separately implantable lead 15 via a connector 8 mounted on the case 18 that houses the generator. The lead 15 itself is of conventional structure, including internal elongate conductors covered with an insulation layer which is biocompatible with the tissue and fluids of the body. At the distal end of the lead, the conductors are electrically connected to a set of electrodes 16 (FIGS. 2, 3). The case 18 is composed of a metal which is biocompatible with the body's tissue and fluids, such as titanium. Electrodes 16 are secured to sites, for example, on adjacent sides of the wall of the large intestine 19 in relatively close proximity to the stomach 20 to sense electrical resistance changes associated with contractions occurring during the normal digestive process. The electrodes may be bipolar or quadripolar, composed of activated iridium, rhodium, or platinum, for example, and preferably having a thin surface layer of iridium oxide to enhance electrical sensitivity. Each of the electrodes may be provided with a biocompatible fabric "collar" or band about the electrode periphery to allow it to be readily sutured in place.

In a quadripolar electrode array, two pairs of electrodes are secured generally in the same plane and normal to the length of the intestinal tract, so that a small signal generated by an appropriately sized generator in the detection circuit and applied across one pair 16-1 can be detected across the other pair 16-2 which is also coupled to the detection circuit. Changes in relative amplitude of the detected signal are proportional to changes in resistance of the signal path. In the digestive process, when contractions occur in the region between the sensing electrodes as a consequence of motility, the resistance in both the signal and sensing paths is reduced. This impedance reduction causes the detected signal to have a higher amplitude than before the contraction, to provide not only an indication of the contraction, but also a measure of the extent of the contraction. The measurement of detected signal strength is made by detection circuit 12. Alternatively, a bipolar electrode pair may be used for both signal application and sensing across the intestine, with the disadvantage of some interference as a result of polarization potentials, which, however, is lessened if the electrodes have an iridium oxide coating.

Detection circuit 12 produces a digital output signal on conductive path 22 for application to logic and control circuit 11 representative of the presence and relative strength of the sensed contractions, if any, at electrodes 16. Circuit 11 is adapted to respond to the output signal from circuit 12, but only if the signal (or absence thereof) occurs (or fails to occur) during a predetermined time-of-day interval when food intake is likely, i.e., corresponding to the patient's normal mealtimes based on circadian rhythm, and the normal digestive process that would produce contractions in the intestinal region where the electrodes are implanted should have commenced. An internal clock 17 which is programmable from an external programmer unit 32, is used to set the predetermined interval, and, by means of an internal crystal oscillator to provide timing signals for the device operation, as well. In this way, stimulus generator 10 may be controlled to selectively deliver a stimulus to the patient's vagus nerve if no signal (indicating no contraction) or a signal representative of only weak contraction(s) is produced by the detection circuit during an initial specified portion of the predetermined mealtime interval.

The same detection system including the lead 15 and electrodes 16 may be used for detecting and treating hypermotility disorders, with the sensing instead, in this case, of abnormally rapid spontaneous contractions of the intestinal tract at the site of the implanted electrodes during the digestive process. The sense signal indicative of such rapid contractions is then used to trigger an output signal from the stimulus generator with electrical parameters programmed to stimulate the vagus nerve in the predetermined manner for treatment of the disorder.

Rather than relying on a type of circadian rhythm function based on time of day of normal food intake by the patient, a separate additional sensing electrode set may be implanted to detect actual food intake by the patient. To that end, a second lead 31 with a substantially identical set of distally-located electrodes 30 (to electrode set 16), and also preferably of the quadripolar type, is implanted in the patient. Lead 31 is also connected at its proximal end to connector 8 of the stimulus generator. In this instance, electrodes 30-1 and 30-2 are secured to opposite sides of the patient's esophagus 36, preferably at a site just above the stomach as shown in FIGS. 2 and 3. Each of the electrodes 30 is provided with a collar for suturing at the selected esophageal locations.

Detection circuit 12 of stimulus generator 10 may comprise conventional detection circuitry associated with quadripolar electrode sensing, including, for example, a peak detector to receive the sensed signal from lead 31 attributable to electrical activity at electrodes 30 (resulting from an injected signal) and the resistance changes resulting from food swallowed by the patient and passing through the esophagus 36 between the electrodes. The peak detector may provide low pass filtering to smooth the detected peaks over a predetermined short time interval of a few seconds. The output of the peak detector may be applied to a comparator, along with an output from a digital-to-analog converter to which digital inputs are supplied by the microprocessor in logic and control circuit 11. The microprocessor receives an input from the comparator and, in turn, supplies an input to internal clock 17 to commence a delay interval related to the timing of the digestive process. At the end of the delay interval, the presence or absence of contractions in the gastrointestinal tract is detected by the circuit that includes electrodes 15. Detection circuit 12 may include a second set of components associated with quadripolar electrodes 15, corresponding to the components and connections described above for receiving the sense signal from electrodes 30, except that in this case the output produced by the microprocessor in response to this contractions-based signal is supplied to output circuit 13.

When activated by the logic and control circuit, output circuit 13 produces a pulsed signal having the desired electrical and timing parameters that have been programmed by the attending physician. The output circuit is connected via an internal conductive path 21 to additional receptacles of connector 8. In FIG. 1, connector 8 is shown in two separate locations, but it will be understood that this depiction is merely for the sake of simplicity in illustrating inputs and outputs of the device. A single connector 8, with an appropriate number of receptacles, is mounted on or integral with the case 18 to accommodate all of the electrical connections to and from internal circuitry of the stimulus generator to receptacles in the connector. A vagal stimulation electrode set 25 at the distal end of another lead 26 is implanted on the patient's vagus nerve 28 (FIG. 3, and in greater detail in FIG. 4), and the proximal end of this lead is inserted into the proper receptacle(s) of the connector for connection to conductive path 21 to receive the stimulating signal from output circuit 13.

The portion of the system external to the patient's body is intended for use by the attending physician to program the implanted device and to monitor its performance. This external portion includes a programming wand 35 which communicates selected parameter values (including changes of values) from the programmer unit 32 to stimulus generator 10 by means of telemetry via an internal antenna 39. The programming wand also accepts telemetry data front the stimulus generator to monitor the performance of the implanted device. This external portion is of the type conventionally employed to program and monitor various implantable medical devices, and its general structure and operation are well known to those skilled in the art. The programmer unit may be implemented as a personal computer with associated monitor 33 and software for performing the functions described above in conjunction with communication between the implanted electronics and the programmer unit (FIG. 2).

The stimulus generator is powered by a battery or battery pack 40 of conventional type such as one or more lithium thionyl chloride cells, having a pair of output terminals electrically connected to the input terminals of a voltage regulator 41. The smooth regulated output voltage may be enhanced by voltage multiplication or division if desired, to power logic and control circuit 11 as well as other electronic components of the implantable device. Programmable parameters of the output signal of the device are controlled by circuit 11. These include current or voltage, frequency, pulse width, on-time, off-time, and start delay time. As a result, the output signal can be configured, selectively, before being applied to lead 26 and via the lead conductors to the electrodes 25 for stimulating the vagus nerve. Tailoring of the signal parameters to the patient's needs produces the desired modulation of the electrical activity of the vagus nerve for treatment and control of the motility disorder of interest.

A reed switch 44 allows the patient to manually activate the implanted device by placing an external magnet (not shown) in close proximity to the device, near the skin, when signs or symptoms indicative of the motility disorder are apparent from the patient's own senses as the digestive process is taking place. Alternative manual activating means suitable for use with the present invention are disclosed in U.S. Pat. No. 5,304,206 of R. Baker, Jr. et al, issued Apr. 19, 1994, assigned to the assignee of this application and incorporated by reference into this specification. Additional details of the structure and operation of the stimulus generator are described in the '172 patent.

In operation of the implanted device, the motility disorder of interest is detected by sensing the presence or absence (as the case may be) of contractions of the gastrointestinal tract at the implant site of electrodes 16 (which may be on the stomach as an alternative to the large intestine). This sensing is limited to a period determined by the patient's circadian cycle and the normal mealtime periods, or by the expiration of the predetermined delay interval following the sensing of food swallowed by the patient and passing through the esophagus at the implant site of electrodes 30. In the latter case, the peak signal amplitude at electrodes 30 is detected and averaged by the peak detector in the detection circuit over a predetermined interval of time selected according to the individual patient's eating habits. The circuit may be calibrated to differentiate between swallowed solids and liquids.

During the predetermined period for detecting a signal from lead 15, detection of presence and frequency (or absence) of intestinal contractions depending on the nature of the motility disorder being treated, results in generation of the programmed pulse signal from the output circuit of stimulus generator 10. The pulse signal is applied to the set of nerve electrodes 25 for stimulating the patient's vagus nerve 28. Patient discomfort may be alleviated by a ramping up the pulses during the first two seconds of stimulation, rather than abrupt application at the programmed level. Additionally, the device may be implemented to permit the patient to interrupt the stimulation by use of the external magnet if the stimulation should produce severe discomfort. The patient would then contact the physician to arrange for reprogramming the output signal level of the device. A conventional clamping circuit (not shown) may be used to limit the maximum voltage (14 volts, for example) deliverable to the vagus nerve, to prevent nerve damage.

The stimulating nerve electrode set 25 is shown in greater detail in FIG. 4. The electrode set is conductively connected to the distal end of a pair of insulated electrically conductors in lead 26. Electrode set 25 includes bipolar stimulating electrodes 25-1 and 25-2, preferably of the type described in U.S. Pat. No. 4,573,481 to Bullara (the '481 patent). The electrode assembly is surgically implanted on the patient's vagus nerve 28 preferably just above the stomach. Electrodes 25-1 and 25-2 are installed on the nerve, and the electrode set is further retained in place by a spiral anchoring tether 46 such as that disclosed in U.S. Pat. No. 4,979,511 to Reese S. Terry, Jr. and assigned to the same assignee as the instant application. Lead 26 is secured in a manner to allow flexing with patient movement, by means of a suture connection 47 to nearby tissue.

The open helical design of electrode set 25 (described in detail in the '481 patent) is self-sizing and flexible, and thus minimizes trauma to the nerve while allowing body fluid interchange with the nerve. The electrode assembly conforms to the shape of the nerve and provides a low stimulation threshold. Structurally, the electrodes are two ribbons of platinum, which may be coated with iridium oxide, individually bonded to the inside surface of respective spiral loops 25-1 and 25-2 of a three-loop helical assembly. The two conductive lead wires are welded to respective ones of these conductive ribbon electrodes. The remaining portion of each loop is silicone rubber, and the third loop 46 is merely the tether. The inner diameter of electrode assembly 25 is approximately two millimeters (mm), and each individual spiral loop is about seven nun long (measured along the axis of the nerve).

FIG. 5 is an idealized representation of the output signal waveform delivered by output circuit 13 of the neurostimulator to electrode set 25. This Figure is especially useful to illustrate the configurable (programmable) parameters on-time, off-time, frequency, pulse width, and output current for the output signal.

For gastric or intestinal hypomotility, typical approximate values of these parameters are pulse frequency: 20 Hz, pulse width: one millisecond (ms), output current: two milliamperes (ma), with ranges from 5 to 50 Hz, 0.1 to 3 ms, and 0.1 to 4 ma, respectively. On-time is in the range from 10 to 600 seconds, with a typical value of 200 seconds, and off-time is in the range from about one minute to twelve hours, with a typical value of four hours. The stimulation increases gastric and intestinal motility by appropriately modulating the electrical activity of the vagus nerve to transmit signals via the vagus projections, which serves to relieve patient discomfort.

In the case of gastric or intestinal hypermotility, the typical approximate values are pulse frequency: 80 Hz, pulse width: one ms, and output current: two ma, with ranges from 5 to 150 Hz, 0.1 to 3 ms, and 0.1 to 4 ma, respectively. The output signal is applied to the nerve continuously for on-time intervals of five minutes and off-time intervals of 30 seconds, with ranges from one to 60 minutes and 10 to 600 minutes, respectively. The effect of this stimulating signal is to inhibit gastric and intestinal motility by modulating the nerve's electrical activity to override signals of the vagus projections, and thereby relieve patient discomfort.

The vagus nerve may have on the order of approximately 100,000 fibers (axons) of three different sizes classified as A, B and C which carry signals to and from the brain and other parts of the body. A and B fibers have a myelin sheath, while the C fibers are unmyelinated. Myelinated fibers are generally larger, conduct faster with lower stimulation thresholds, and exhibit a particular strength-duration curve in response to a specific width and amplitude of stimulation pulse, as compared to unmyelinated fibers. A and B fibers can be stimulated with relatively narrow pulse widths, from 50 to 200 micro-seconds (µs), for example. C fibers typically require wider pulse widths (e.g., 300–1000 µs) and higher amplitudes for activation. Thus, A and B fibers can be stimulated without stimulating C fibers.

Electrical stimulation of nerve fibers typically causes neural signals to flow in both directions, but in the vagus nerve each axon exhibits only unidirectional electrical conduction in normal circumstances. According to the scientific literature, the vagus nerve is composed of somatic and visceral afferents (inward conducting nerve fibers that convey impulses toward a nerve center such as the brain or spinal cord) and efferents (outward conducting nerve fibers that convey impulses to an effector to stimulate it and produce activity). Most vagal nerve fibers are of the C type, principally visceral afferents having cell bodies lying in masses or ganglia in the neck. The central projections terminate in the nucleus of the solitary tract which sends fibers to various regions of the brain, including the hypothalamus, thalamus, and amygdala. Others continue to the medial reticular formation of the medulla, the cerebellum, the nucleus cuneatus and other regions.

By appropriately setting pulse width and amplitude of the electrical signal delivered to the vagus nerve, the nerve fibers can be selectively stimulated, such as A and not B and C; or A and B, but not C; or A, B and C.

Various related factors may need to be considered in the programming process, such as use of the knowledge that C fibers conduct signals very slowly to recognize that they will not be highly responsive to attempts at rapid stimulation, and thus that a short pulse train should be used. The fibers would become refractory to stimulation within a relatively short time interval and thus incapable of tracking the pattern of a longer pulse train. After a suitable recovery period, another short pulse train may be applied to achieve further treatment. The precise pattern to be used, e.g., the length of the time intervals on and off, will depend on and be adjusted to the individual patient.

FIG. 6 is a flow chart illustrating the device-implemented method of treating and controlling the motility disorder of interest, and is self-explanatory.

Although certain preferred embodiments and methods of treating and controlling chronic motility disorders through modulation of the electrical activity of the patient's vagus nerve have been described herein, it will be apparent to those skilled in the art, from the foregoing description, that variations and modifications of the preferred embodiments, methods and techniques may be made without departing from the true spirit and scope of the invention.

For example, the stimulus generator may be external to the patient's body, with only an RF coil, rectifier and the lead/nerve electrode assembly implanted; or with the lead implanted percutaneously through the skin and to the nerve electrode. Special care would need to be taken to prevent potential infection via the path external to the body to the nerve along the lead. Advantageously, however, the patient can be subjected to a relatively simple procedure to determine whether the motility disorder of this particular patient is responsive to treatment by this method. If it is, a permanent implant may be provided. Disadvantages of the partially implanted device are the inconvenience of carrying the external transmitter on the patient's person, and the requirement of greater power for activation than if the system were totally implanted.

Accordingly, it is intended that the invention shall be limited only to the extent required by the appended claims and the rules and principles of applicable law.

What is claimed is:

1. A method of treating patients suffering from motility disorders, comprising the steps of:

sensing a prescribed event indicative of an imminent need for treatment of a specific motility disorder of interest, and responding to the sensed occurrence of the prescribed event by applying a stimulating electrical signal having predetermined electrical parameters to the patient's vagus nerve to modulate the electrical activity of the vagus nerve in a manner to produce a reaction in the patient's gastrointestinal tract by which to alleviate the motility disorder of interest.

2. The method of claim 1, wherein:

the prescribed event is inadequate contractions of at least a predesignated portion of the patient's gastrointestinal tract compared with a range of contractions observed in human digestive systems deemed to be normal, within a predetermined interval of time following consumption of food by the patient.

3. The method of claim 2, wherein:

the predesignated portion of the patient's gastrointestinal tract is the stomach.

4. The method of claim 1, wherein:

the prescribed event is onset of excessively rapid contractions of at least a predesignated portion of the patient's gastrointestinal tract compared with speed of contractions observed in human digestive systems deemed to be normal, within one of (i) a predetermined interval of time following consumption of food by the patient, and (ii) a predetermined interval of time without consumption of food by the patient.

5. The method of claim 4, wherein:

the predesignated portion of the patient's gastrointestinal tract is the stomach.

6. The method of claim 1, wherein:

the prescribed event is sensing by the patient of symptoms of the motility disorder of interest, and the response is the patient's own recognition of the need for treatment by voluntarily initiating the application of said stimulating electrical signal to the vagus nerve.

7. The method of claim 1, wherein:

said stimulating signal is applied to the patient's vagus nerve by application to a nerve electrode implanted on the vagus nerve in the vicinity of the patient's stomach.

8. Apparatus for treating patients with motility disorders by application of a modulating signal to the patient's vagus nerve to stimulate or inhibit neural impulses and produce excitatory or inhibitory neurotransmitter release by the nerve according to the specific nature of the motility disorder, comprising:

neurostimulator means for generating an electrical output signal in response to activation thereof, said neurostimulator means including sensing means for detecting the occurrence of a selected event indicative of the need for imminent treatment of the motility disorder, and including activating means responsive to the detection for activating said neurostimulator means, and lead/electrode means responsive to generation of the electrical output signal by said neurostimulator means for application thereof as said modulating signal to the patient's vagus nerve.

9. The apparatus of claim 8, wherein:

said neurostimulator means further includes:

programming means for selectively programming the parameters of the electrical output signal of said neurostimulator means according to the nature of the motility disorder being treated, within respective predetermined ranges.

10. The apparatus of claim 8, wherein:

said neurostimulator memos further includes:

means for calibrating the neurostimulator means according to the specific patient and the specific motility disorder being treated.

11. The apparatus of claim 8, wherein:

the motility disorder being treated is hypomotility, and said sensing means comprises impedance detecting means responsive to an absence of contractions of specified magnitude in the gastrointestinal system of the patient within a predetermined interval of time after consumption of food by the patient as the event to be detected.

12. The apparatus of claim 8, wherein:

the motility disorder being treated is hypermotility, and said sensing means comprises impedance detecting means responsive to contractions in the gastrointestinal system of the patient despite an absence of consumption of food by the patient within a predetermined interval of time prior to the onset of said contractions as the event to be detected.

13. The apparatus of claim 8, wherein:

said sensing means comprises means for detecting voluntary triggering of said activating means by the patient as the event to be detected.

14. The apparatus of claim 8, wherein:

said lead/electrode means includes nerve electrode means and means for securing said nerve electrode means to the patient's vagus nerve in the vicinity of the stomach.

15. The apparatus of claim 8, wherein:

said neurostimulator means is arranged and adapted to be implanted in the patient's body.

16. A method of treating a patient suffering from a motility disorder in which a medical therapeutic device is implanted in the patient's body, comprising the device-implemented steps of:

detecting a response of the patient's gastrointestinal (GI) tract to consumption of food by the patient which is abnormal relative to predetermined normal human digestive processes and is indicative of a need for treatment to alleviate a motility disorder of interest, and after detecting the abnormal response, applying to the patient's vagus nerve an electrical stimulus configured to modulate the electrical activity of the nerve such that the motility disorder of interest is alleviated.

17. The method of claim 16, further including the step of delaying the detecting step until the expiration of a predetermined interval of time from initial consumption of the food.

18. The method of claim 16, wherein:

the abnormal response to be detected is preselected to consist of abnormally slow contractions of the patient's GI tract where the patient is suffering from hypomotility, and abnormally rapid contractions of the patient's GI tract where the patient is suffering from hypermotility.

19. The method of claim 18, wherein:

the detecting step is performed by sensing electrical phenomena indicative of presence or absence of contractions of the patient's stomach.

20. The method of claim 18, wherein:

the detecting step is performed by sensing electrical phenomena indicative of presence or absence of contractions of the patient's large intestine.

21. The method of claim 16, wherein:

the electrical stimulus is configured as a pulsed signal by programming parameters of the signal including on-time, off-time, frequency, pulse width, and current.

* * * * *